US009144459B2

(12) United States Patent
Surti et al.

(10) Patent No.: US 9,144,459 B2
(45) Date of Patent: Sep. 29, 2015

(54) ENDOSCOPIC ULTRASOUND ABLATION NEEDLE

(75) Inventors: Vihar Surti, Winston-Salem, NC (US); John Sigmon, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 448 days.

(21) Appl. No.: 13/553,158

(22) Filed: Jul. 19, 2012

(65) Prior Publication Data

US 2014/0025054 A1 Jan. 23, 2014

(51) Int. Cl.
| | |
|---|---|
| *A61B 18/18* | (2006.01) |
| *A61B 18/14* | (2006.01) |
| *A61N 7/00* | (2006.01) |
| *A61B 18/00* | (2006.01) |
| *A61B 19/00* | (2006.01) |

(52) U.S. Cl.
CPC ..... *A61B 18/1492* (2013.01); *A61B 2018/0016* (2013.01); *A61B 2018/00029* (2013.01); *A61B 2018/00196* (2013.01); *A61B 2018/00267* (2013.01); *A61B 2018/00577* (2013.01); *A61B 2018/00994* (2013.01); *A61B 2018/1437* (2013.01); *A61B 2018/1465* (2013.01); *A61B 2018/1467* (2013.01); *A61B 2019/5276* (2013.01); *A61B 2019/5425* (2013.01); *A61N 7/00* (2013.01); *A61N 2007/0043* (2013.01)

(58) Field of Classification Search
USPC .................................................... 606/16, 41
See application file for complete search history.

(56) References Cited

U.S. PATENT DOCUMENTS

| | | |
|---|---|---|
| 4,494,539 A | 1/1985 | Zenitani et al. |
| 4,627,838 A | 12/1986 | Cross et al. |
| 4,633,880 A | 1/1987 | Osypka et al. |

(Continued)

FOREIGN PATENT DOCUMENTS

| | | |
|---|---|---|
| WO | WO 00/01313 A1 | 1/2000 |
| WO | WO 03/026525 A1 | 4/2003 |
| WO | WO 03/089997 A2 | 10/2003 |

OTHER PUBLICATIONS

International Search Report and Written Opinion of the International Searching Authority for International Application No. PCT/US2013/049680, dated Oct. 18, 2013, 11 pages.

(Continued)

*Primary Examiner* — Carl H Layno
*Assistant Examiner* — Jennifer Ghand
(74) *Attorney, Agent, or Firm* — Brinks Gilson & Lione

(57) ABSTRACT

A radiofrequency tissue ablation device includes an elongate outer cannula having proximal and distal ends and an intermediate length therebetween where a longitudinal region of the intermediate length is configured as an ablation electrode. A cannula lumen extends longitudinally through the cannula. A stylet extends slidably through the lumen and is secured to the cannula between the ablation electrode and the cannula distal end. The ablation electrode includes a plurality of substantially parallel helical apertures disposed around and extending through a cannula circumference. The ablation electrode is configured to be circumferentially expandable such that in a first state, it is essentially cylindrical with a substantially uniform outer diameter along substantially its entire length, and in a second state, its parallel helical apertures are expanded such that the intervening portions of the cannula form an outer diameter greater than the outer diameter of cannula portions proximal and distal of the electrode.

19 Claims, 3 Drawing Sheets

(56) References Cited

U.S. PATENT DOCUMENTS

| | | | |
|---|---|---|---|
| 5,328,453 A | 7/1994 | Sibalis | |
| 5,476,481 A | 12/1995 | Schöndorf | |
| 5,536,267 A | 7/1996 | Edwards et al. | |
| 5,567,413 A | 10/1996 | Klaveness et al. | |
| 5,702,359 A | 12/1997 | Hofmann et al. | |
| 5,782,899 A * | 7/1998 | Imran | 607/122 |
| 5,794,626 A | 8/1998 | Kieturakis | |
| 5,800,484 A | 9/1998 | Gough et al. | |
| 5,827,276 A | 10/1998 | LeVeen et al. | |
| 5,855,576 A | 1/1999 | LeVeen et al. | |
| 5,857,992 A | 1/1999 | Haak et al. | |
| 5,873,849 A | 2/1999 | Bernard | |
| 5,967,977 A * | 10/1999 | Mullis et al. | 600/380 |
| 5,993,434 A | 11/1999 | Dev et al. | |
| 6,033,397 A | 3/2000 | Laufer et al. | |
| 6,161,047 A | 12/2000 | King et al. | |
| 6,200,314 B1 | 3/2001 | Sherman | |
| 6,235,023 B1 | 5/2001 | Lee et al. | |
| 6,258,086 B1 | 7/2001 | Ashley et al. | |
| 6,278,895 B1 | 8/2001 | Bernard | |
| 6,418,341 B1 | 7/2002 | Hofmann et al. | |
| 6,889,089 B2 | 5/2005 | Behl et al. | |
| 6,997,885 B2 | 2/2006 | Lubock et al. | |
| 7,097,643 B2 | 8/2006 | Cornelius et al. | |
| 7,113,821 B1 | 9/2006 | Sun et al. | |
| 7,182,761 B2 | 2/2007 | Garabedian et al. | |
| 7,306,595 B2 | 12/2007 | Ostrovsky et al. | |
| 7,309,336 B2 | 12/2007 | Ashley et al. | |
| 7,344,518 B2 | 3/2008 | McGuckin, Jr. et al. | |
| 7,344,533 B2 | 3/2008 | Pearson et al. | |
| 7,376,468 B2 | 5/2008 | King et al. | |
| 7,399,299 B2 | 7/2008 | Daniel et al. | |
| 7,412,285 B2 | 8/2008 | Schroeppel et al. | |
| 7,419,487 B2 | 9/2008 | Johnson et al. | |
| 7,431,720 B2 | 10/2008 | Pendekanti et al. | |
| 7,447,551 B2 | 11/2008 | Kuo et al. | |
| 2001/0001819 A1 | 5/2001 | Lee et al. | |
| 2001/0012956 A1 | 8/2001 | Behl et al. | |
| 2002/0068879 A1 * | 6/2002 | Lubock et al. | 600/567 |
| 2002/0087112 A1 | 7/2002 | Constantz et al. | |
| 2003/0083681 A1 | 5/2003 | Moutafis et al. | |
| 2003/0125660 A1 | 7/2003 | Moutafis et al. | |
| 2004/0025556 A1 | 2/2004 | Klint et al. | |
| 2004/0236320 A1 | 11/2004 | Protsenko et al. | |
| 2005/0165393 A1 | 7/2005 | Eppstein | |
| 2005/0177105 A1 | 8/2005 | Shalev | |
| 2005/0182449 A1 | 8/2005 | Auge, II et al. | |
| 2005/0197571 A1 | 9/2005 | McVeigh | |
| 2005/0222646 A1 | 10/2005 | Kroll et al. | |
| 2005/0288730 A1 | 12/2005 | Deem et al. | |
| 2006/0111705 A1 | 5/2006 | Janzen et al. | |
| 2006/0217704 A1 | 9/2006 | Cockburn et al. | |
| 2006/0247530 A1 | 11/2006 | Hardin, Jr. et al. | |
| 2007/0156130 A1 | 7/2007 | Thistle | |
| 2007/0185484 A1 | 8/2007 | Randall | |
| 2012/0053576 A1 | 3/2012 | Thistle | |
| 2013/0317339 A1 * | 11/2013 | Waldstreicher et al. | 600/409 |

OTHER PUBLICATIONS

International Search Report for PCT Application No. PCT/US2002/31006, date of mailing May 12, 2012, 3 pgs.

* cited by examiner

ENDOSCOPIC ULTRASOUND ABLATION NEEDLE

TECHNICAL FIELD

Embodiments disclosed herein generally relate to tissue ablation devices. More particularly, the embodiments disclosed relate to endoscopic ablation devices navigable with ultrasound visualization.

BACKGROUND

Commonly used open surgical procedures such as tissue resection for use in treatment of benign and malignant tumors of the liver and other organs have several key shortcomings affecting efficacy, morbidity and mortality. In many cases, open surgical resection may carry risks of complication that are not justified by potential benefit, or they may not be practically possible due to anatomical limits on access to the target tissue. To help overcome these limitations, some percutaneous mono-polar radio frequency (RF) devices have been used in tissue ablation and resection. These mono-polar devices carry their own risks and limitations known in the art. There is a need for tissue ablation systems that overcome the shortcomings of open surgery techniques and existing percutaneous devices.

It may be desirable to provide an endoscopically deployable tissue ablation device that can be navigated under ultrasound and/or fluoroscopy. Such devices may be operable through minimally-invasive surgical endoscopes (e.g., gastrointestinal endoscopes, other endoscopes using natural body orifices, and/or laparoscopes that utilize only small percutaneous access openings).

BRIEF SUMMARY

In one aspect, embodiments disclosed herein may include an endoscopic tissue ablation device, as well as methods for using same in a patient. Some embodiments of a radiofrequency tissue ablation device may include: an elongate outer cannula including a cannula proximal end, a cannula distal end, and a cannula intermediate length between the proximal end and distal end, where a longitudinal region of the intermediate length near the distal end is configured as an ablation electrode and including a cannula lumen extending longitudinally through the length of the cannula; and an elongate stylet extending slidably through the cannula lumen and secured to the cannula between the ablation electrode and the cannula distal end; where the ablation electrode includes a plurality of substantially parallel helical apertures disposed around a circumference of the outer cannula, the apertures extending through the cannula; where the ablation electrode is configured to be circumferentially expandable such that in a first state, when the distal cannula end is disposed at a maximum device-length distance from the proximal cannula end, the outer cannula is essentially cylindrical with a substantially uniform outer diameter along substantially its entire length; and in a second state, when the stylet and the secured cannula distal end are less than a maximum device-length distance from the proximal cannula end, the substantially parallel helical apertures of the ablation electrode are expanded and the intervening portions of the cannula form an outer diameter greater than the outer diameter of cannula portions proximal of and distal of the ablation electrode.

DETAILED DESCRIPTION

Figure 1:
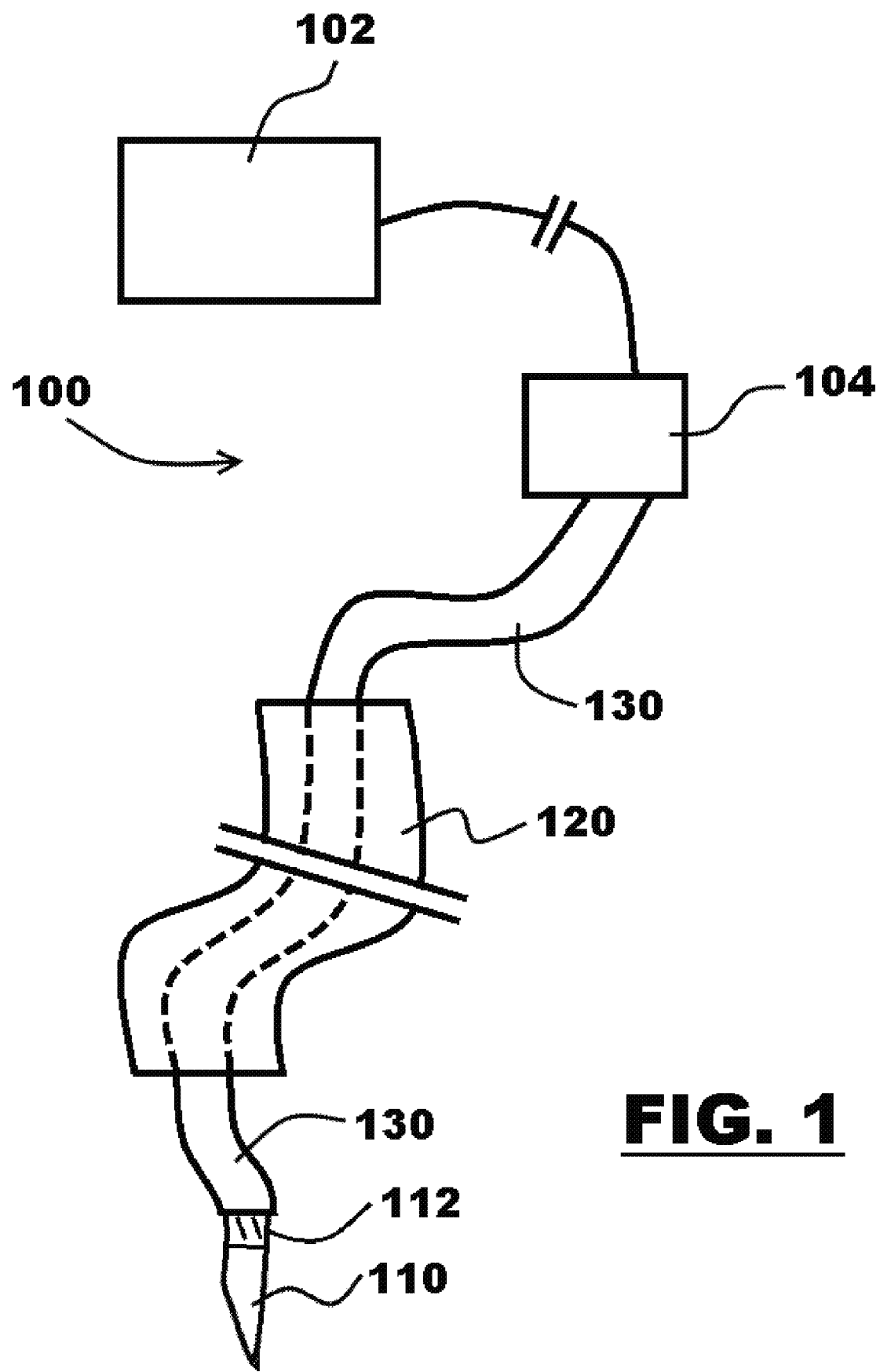
FIG. 1 shows a diagrammatically simplified of one embodiment of a tissue ablation system.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

One embodiment of a tissue ablation system 100 is described with reference to FIG. 1, which diagrammatically illustrates a general set-up including an ablation energy source 102, an optional separate control unit 104 (that, if present, may provide separate and/or more device-local control of ablation energy), a tissue ablation device 110 extending through (and/or including) a sheath 130 and including an ablation structure 112 through which energy is released to target tissue, and an optional endoscope 120 through which the tissue ablation device is slidably operable. It should be appreciated that this diagrammatic representation is not to scale and is intended only to show one potential orientation of certain embodiments and/or components of embodiments.

Those of skill in the art will appreciate that the ablation energy source may take a variety of forms. Certain embodiments below are described with reference to a radiofrequency (RF) ablation device, but those of skill in the art will be enabled, with reference to the current disclosure and the state of the art, to construct and operate devices within the scope of the present disclosure that use non-RF energy in addition to or instead of RF energy to provide for tissue ablation.

For example, the energy source may be embodied as a microwave power source 102 coupled to a microwave antenna 112 including a plurality of parallel helical struts providing microwave energy in a frequency range—for example—from about 915 MHz to about 2.45 GHz. As another example, the energy source may be embodied as a radio-frequency (RF) power source 102 coupled to an RF electrode 112 embodied as a plurality of helical struts. As another example, the energy source may be embodied as a coherent light source 102 coupled to an ablation structure embodied a plurality of optical fibers or light pipes 112 oriented as parallel helical yet another example, the energy source may be embodied as n incoherent light source 102 coupled to a plurality of optical fibers 112 oriented as parallel helical struts. As still another example the energy source may be embodied as a source 102 of heated fluid coupled in fluid communication with a tubular ablation structure 112 with a closed or at least partially open lumens configured to receive the heated fluid (configured and operated with sufficient energy capacity to effect ablation of target tissue), configured as parallel helical struts. As still yet another example, the energy source may be embodied as a cooled fluid source 102 coupled in fluid communication with a tubular ablation structure 112 with a closed or at least partially open lumens configured to receive the cooled fluid (configured and operated with sufficient energy capacity to effect ablation of target tissue, such as—for example—a cryogenic fluid) and configured as parallel helical struts. As resistive heating source 102 coupled to a plurality of alternating current (A/C) conductive wires 112 configured as parallel helical struts. As still another example, the energy source may be embodied as an ultrasound power source 102 coupled to an ultrasound emitter 112 oriented as parallel helical struts, wherein the ultrasound power source produces ultrasound energy—for example—in the range of about 300 kHz to about 3 GHz. $_{[tkc1]}$Any operable combinations thereof may be practiced within the scope of the present invention, where the ablation structure 112 includes a generally helical strut configuration as described below. Of course, those of skill in the art will appreciate that the absolute and relative dimensions of such alternative embodiments will impose certain practical limitations thereupon.

Figure 2A:
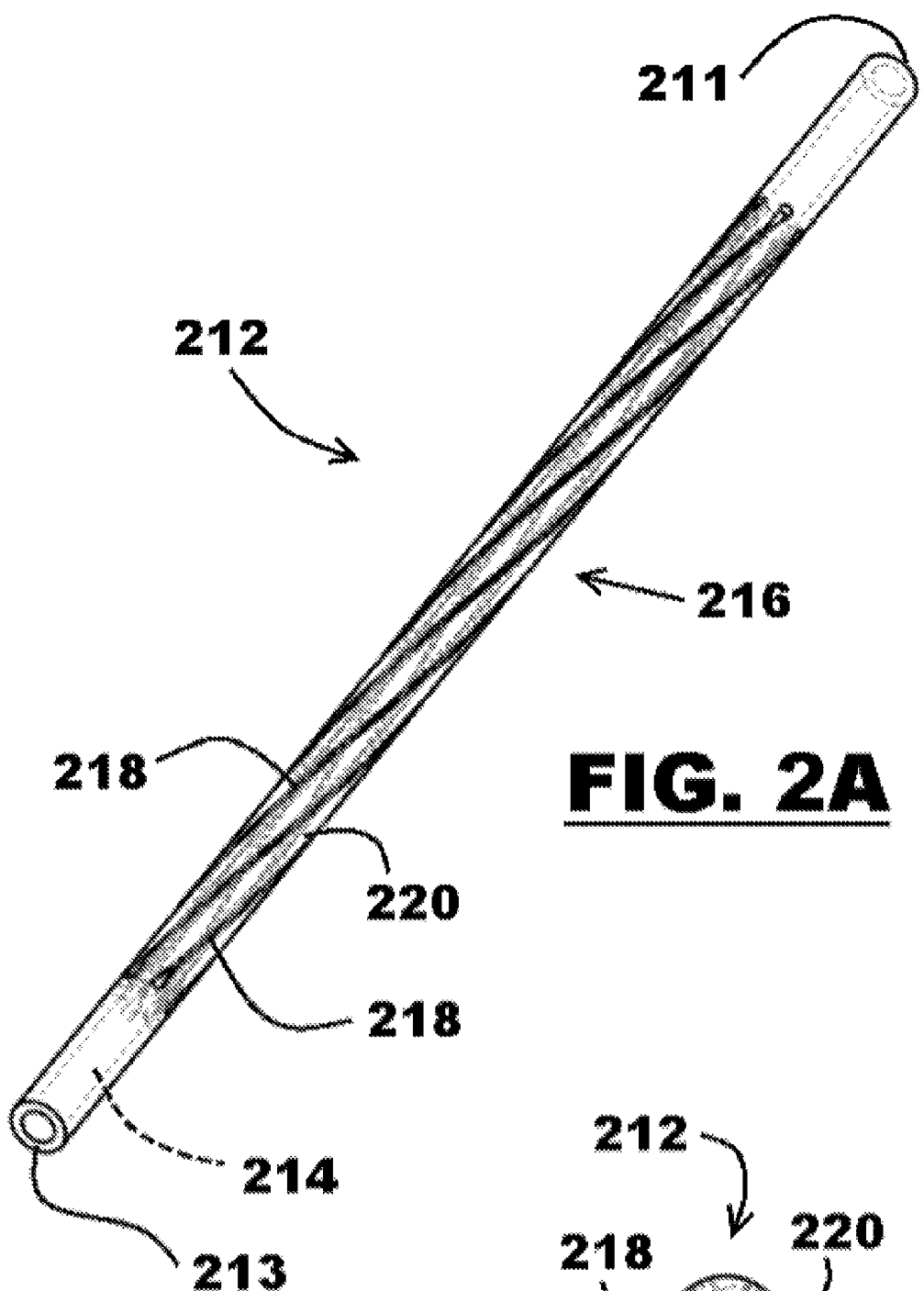
FIGS. 2A and 2B illustrate a radially expandable elongate cannula of a tissue ablation device embodiment.
Figure 2B:
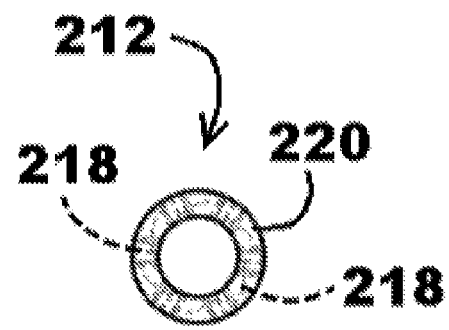

FIGS. 2A and 2B illustrate an elongate cannula 212 of a tissue ablation device. The cannula 212 may include a metallic or other construction material configured to transmit RF energy or other tissue-ablating energy. The cannula 212 has a tubular body construction that includes a cannula lumen 214 extended longitudinally through its length. A central body region 216 of the cannula 212 includes a plurality of helical apertures configured as slits 218 that extend through the body wall into the cannula lumen 214. In the embodiment shown, the plurality of slits 218 are substantially parallel and of substantially equal length. As few as two apertures may be provided, but one preferred embodiment includes six apertures.

As shown in the side view of FIG. 2A, and more clearly in the end-on view of FIG. 2B, the embodiment illustrated includes six apertures 218, which longitudinally/laterally define six intervening flexible struts 220. Each of the apertures 218 and struts 220 traces a complete rotation around the cannula's outer circumference along the length of that aperture/strut. When the cannula 212 is longitudinally linearly compressed, the struts 220 are configured with sufficient flexibility to expand away from each other and flare outward. In the embodiment of FIGS. 2A-2B, these struts 220 may serve as an ablation electrode that—when conducting RF energy and in contact with target tissue—will provide ablation of that target tissue. As such, together, the apertures 218 and struts 220 form an ablation structure portion of the cannula 212.

Stated differently, the ablation structure including the apertures 218 and struts 220 is configured to be circumferentially expandable. In a first state, when the distal cannula end 213 is disposed at a maximum device-length distance from the proximal cannula end 211, the outer cannula 212 is essentially cylindrical with a substantially uniform outer diameter along substantially its entire length. In a second state, when the cannula distal end is less than a maximum device-length distance from the proximal cannula end, the substantially parallel helical apertures 218 are expanded and the intervening portions 220 of the cannula 212 form an outer diameter greater than the outer diameter of cannula portions proximal of and distal of the ablation structure portion's length. The second state may include a single expanded state, or it may include a plurality of expanded states that can be step-wise/incremental in discreet separate outer diameters, or than can be more continuous (e.g., smoothly transitioning between smaller/larger diameters). Certain preferred embodiments will include discreet outer diameter increments that may be selected by a user actuating a proximal control.

The cannula 212 is shown with a rounded, generally atraumatic distal end 213. In other embodiments, a penetrating distal end tip (e.g., a needle-point configuration using any tissue-penetrating tip-configuration known or developed in the art. A non-penetrating tip may be useful for some applications including directing the cannula 212 out of an endoscope, or without an endoscope in/through a patient's esophagus (e.g., to ablate tissue associated with Barrett's esophagus) or other body passages. Embodiments that include a tissue-penetrating tip may be useful in NOTES (natural orifice transesophageal surgery) techniques, and/or other techniques for endoscopic or non-endoscopic access to internal organs. For example, a trans-esophageal endoscopic procedure may be used where the cannula is directed through an endoscope to an intragastric or intraduodenal location where it is used to penetrate through the wall of the alimentary canal into a target site in a patient's liver or other target location. The device may be configured for percutaneous use (e.g., in an interventional radiology or other application).

In this and other embodiments, an outer surface of the cannula body 212 may dimpled or provided with other surface (or embedded) structural features to enhance its ability to reflect ultrasound waves and thereby provide a desirable echogenic profile. This dimpled characteristic may be embodied as a different irregular, patterned, or textured surface feature (e.g., knurled, ribbed) that may enhance the echogenicity of the cannula 212, which will aid in visualizing it during ultrasound-guided placement, and allow it to be used in ultrasound visualization of a target site (e.g., a tumor mass). Other echogenic enhancements may be provided in addition to, or instead of, the dimpling. For example, certain echogenic polymers may be used in the cannula construction, or as a coating of a metal cannula. Other echogenic enhancements known in the art may be implemented within the scope of the claims. The dimpled or otherwise echogenically-enhanced region preferably will include a distal needle end region, while a more proximal length of the needle may be free of dimples and/or other echogenicity-enhancing features. This feature may enhance navigability and/or reduce the fluoroscopy exposure needed during a procedure.

Figure 3:
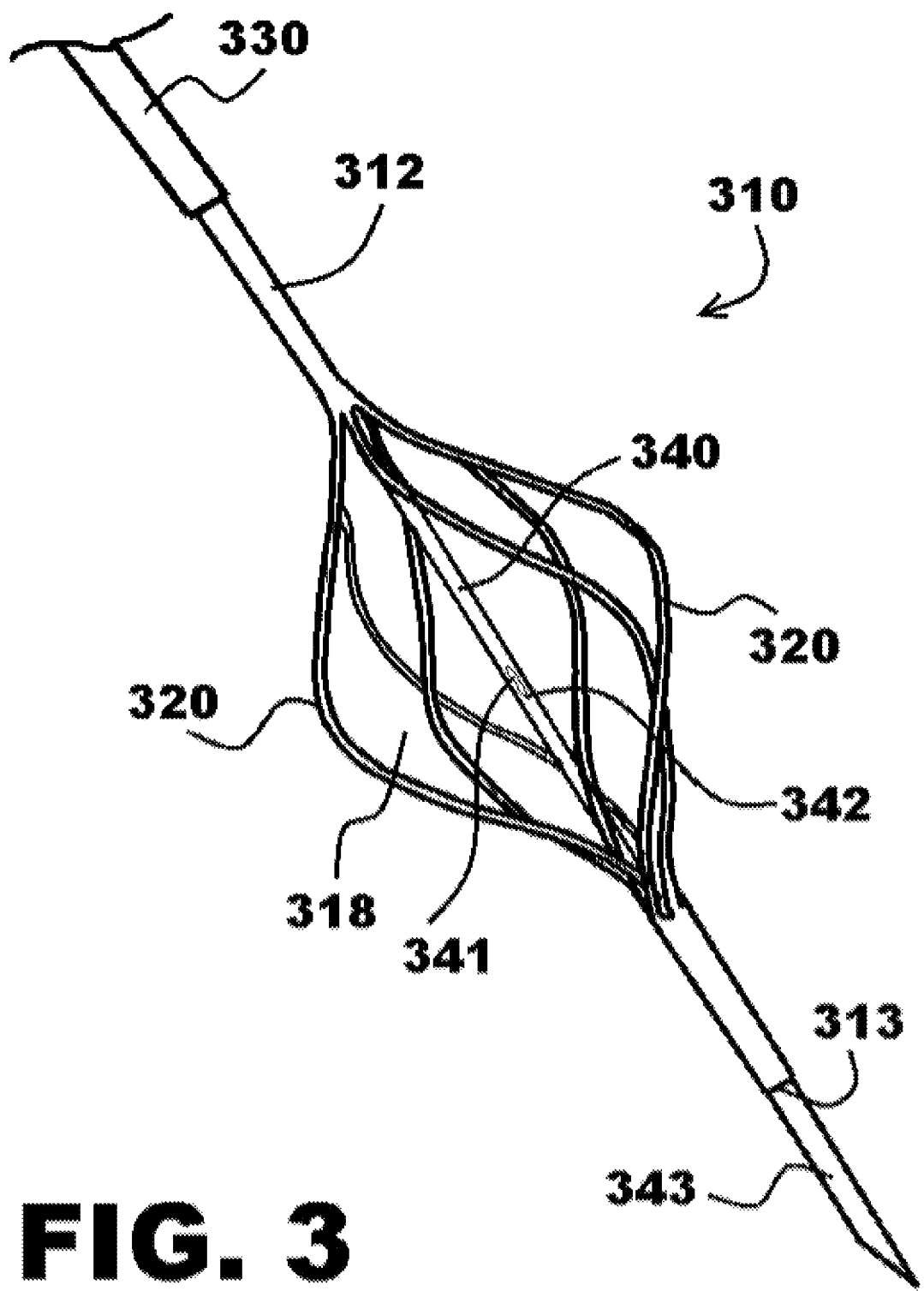
FIG. 3 shows a radially-expanded distal portion of one embodiment of a tissue ablation system.

FIG. 3 shows a distal portion of a tissue ablation device 310. The device 310 includes a cannula 312 constructed in the same manner as described above with reference to cannula 212 of FIGS. 2A-2B. The device 310 also includes an elongate introducer sheath 330, within which the cannula 312 may remain while it is directed, for example, through a working channel of an endoscope or a patient body lumen so that the cannula's penetrating distal tip 313 is not damaged by (and does not penetrate into) a surface thereof. The cannula 312 may be slidably located in the sheath 330, and it is shown in FIG. 3 as being extended therefrom. In certain preferred embodiments, a proximal end or end portion of the cannula may be affixed to or engageable to the sheath in a manner that will allow the stylet (and distal cannula portion affixed thereto) to move slidably relative to the proximal cannula end in a manner facilitating expansion of the apertures 318 and struts 320. Those of skill in the art will readily appreciate that a variety of handle designs are well-known that will be operable to control this function and the functions described below. For example handle designs used with the COOK Echo-Tip® products may readily be useful with the presently disclosed configurations.

The cannula lumen (not shown) is at least partially lengthwise occupied by a stylet 340. The stylet 340 is affixed to the cannula portion distal of the apertures 318 and struts 320. Specifically, in some embodiments the elongate stylet extends slidably through the proximal length of the cannula lumen and is secured to the cannula 312 between the ablation portion and the cannula distal end 313. In the embodiment illustrated, the stylet distal end 343 includes a penetrating tip that extends beyond the cannula distal end 313. Whether or not the cannula includes echogenicity-enhancing features as described above, the stylet may include one or more echogenicity-enhancing features to provide for ultrasound location and/or navigation. It may also include a stylet lumen 341, partially visible through a stylet aperture 342, extending through its length (which may facilitate, e.g., wire-guide directed navigation, and/or passage for irrigation fluid to a region external of the stylet and adjacent to the ablation portion of the cannula).

The ablation portion including the apertures 318 and struts 320 is configured to be circumferentially expandable such that in a first state, when the distal cannula end 313 is disposed at a maximum device-length distance from the proximal cannula end (not visible in FIG. 3), the outer cannula 312 is essentially cylindrical with a substantially uniform outer diameter along substantially its entire length. In a second state, when the stylet 340, and the cannula distal length secured thereto, are less than a maximum device-length distance from the proximal cannula end, the substantially parallel helical apertures 318 of the ablation portion are expanded and the intervening portions 320 of the cannula 312 form an outer diameter greater than the outer diameter of cannula portions proximal of and distal of the ablation portion. This provides for the ablation portion to contact and even penetrate tissue during provision of ablation energy through the ablation portion. This second state may be effected by having a proximal region of the cannula 312 affixed to the sheath and executing one or both of: retracting the stylet proximally relative to the sheath and extending the sheath distally relative to the stylet.

The stylet and/or the outer cannula may be insulated in a manner that prevents transmission of RF energy or other energy therebetween. For example, an RF energy generator may be provided that is in electronic or other RF-transmitting communication with the cannula, but not the stylet. Whether insulated or not, the cannula of each embodiment most preferably is configured to transmit RF or other energy sufficient to necrotize animal tissue for the purpose of ablation.

The helical configuration described herein provides several advantages that were surprising to the inventors. In particular, the generally helical orientation of the struts provides superior performance over struts or wires that are longitudinally aligned with and parallel to a central longitudinal cannula access. This is particularly true when the struts are expanded to displace and/or move radially through fibrotic tissue, where their structure provides desirable mechanical advantage. It should be noted that the cut apertures/struts of the present disclosure are intended to include spaced wires that are helically oriented. For example, while referring to a cannula (e.g., laser-cut) with alternating apertures and struts, the present disclosure intends those terms to include a cannula that includes a portion defined by helically wound wires that will behave in an equivalent manner.

In one preferred embodiment, the ablation portion is attached to an RF energy source and is configured to operate as an RF electrode. In a preferred method of treatment, the ablation portion (e.g., including struts 320) will be directed into a target site such as—for example—a tumor mass. A low-energy RF field will be generated to cause slow tissue necrosis (rather than a high-energy cutting and coagulation RF energy supply). The cannula will be foreshortened to expand the struts and enlarge the RF field and volume of tissue being ablated.

In one embodiment, the outer cannula 312 may be configured as a 19-gauge nitinol cannula, and the stylet 340 may be configured as a stainless steel endoscopic ultrasound needle including one or more echogenicity-enhancing surface dimpling. In another embodiment, a cannula (e.g., like cannula 212) may be configured as, for example, a 22-gauge nitinol cannula, which may be about 0.9 inches (about 2.3 cm) in length from its proximal end to its distal end; the length (linearly along the longitudinal cannula axis) of each aperture and strut may be about 0.7 inches (about 1.7 cm), generally centered between the proximal and distal cannula ends; the apertures may be laser-cut with radiused ends, each about 0.003 inches (about 0.008 cm) wide, and each tracing a full 360° rotation along its length. In an embodiment with six symmetrically-spaced apertures, a first edge of each aperture will be radially spaced from the first edge of an adjacent aperture by about 60°. In different embodiments, the pitch of each aperture and slit may vary, but preferred embodiments may generally include a pitch of less than 45°, in order to preserve lateral expansion during linear compression. However, other pitches may be used, and those of skill in the art will appreciate that rotating the distal cannula portion while longitudinally/ linearly compressing it to expand the apertures may provide desirable radial expansion. It should also be appreciated that cannula sizes may range in various embodiments from 18-gauge to 25-gauge (that is, between about 18 and about 25 gauge, inclusive of those gauges and any legal equivalents).

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:
1. A radiofrequency tissue ablation device comprising:
   an elongate outer cannula including a cannula proximal end, a cannula distal end, and a cannula intermediate length between the proximal end and distal end, where a longitudinal region of the intermediate length near the distal end is configured as an ablation electrode and including a cannula lumen extending longitudinally through the length of the cannula; and
   an elongate stylet extending slidably through the cannula lumen and secured to the cannula between the ablation electrode and the cannula distal end;

where the ablation electrode includes a plurality of substantially parallel helical apertures disposed around a circumference of the outer cannula, the apertures extending through the cannula;

where the ablation electrode is circumferentially expandable such that in a first state, when the distal cannula end is disposed at a maximum device-length distance from the proximal cannula end, the outer cannula is essentially cylindrical with a substantially uniform outer diameter along substantially its entire length; and in a second state, when the stylet and the secured cannula distal end are less than a maximum device-length distance from the proximal cannula end, the substantially parallel helical apertures of the ablation electrode are expanded and intervening portions of the cannula form an outer diameter greater than the outer diameter of cannula portions proximal of and distal of the ablation electrode.

2. The device of claim 1, where the outer cannula includes surface structure configured to enhance its echogenicity.

3. The device of claim 1, where the outer cannula, the stylet, or a combination thereof provides a penetrating distal tip.

4. The device of claim 1, where the plurality of substantially parallel helical apertures is configured as six slits of substantially equal length, each of which extends through the cannula from the cannula's exterior surface to the cannula lumen.

5. The device of claim 1, where the stylet is insulated relative to the outer cannula such that the radiofrequency energy transmitted through the outer cannula is not contact-communicated to the stylet.

6. The device of claim 1, where the stylet includes a stylet lumen extending through at least a portion of its length.

7. The device of claim 6, where the stylet lumen is disposed in fluid communication with at least one stylet aperture underlying the ablation electrode region and configured to communicate irrigation fluid to a region external of the stylet and adjacent to the ablation electrode.

8. The device of claim 1, where the outer cannula is configured as a helically-cut nitinol cannula.

9. The device of claim 1, where the stylet is configured as an endoscopic ultrasound needle including a penetrating distal tip and at least one echogenicity-enhancing structural feature.

10. The device of claim 1, where the outer cannula is configured as a nitinol cannula between 18-gauge and 25-gauge, and the stylet is configured as a stainless steel endoscopic ultrasound needle including one or more echogenicity-enhancing surface features.

11. The system of claim 1, further comprising a radiofrequency energy generator in electronic communication with the ablation electrode.

12. A tissue ablation device comprising:

an elongate outer cannula including a cannula proximal end, a cannula distal end, and a cannula intermediate length between the proximal end and distal end, where a longitudinal region of the intermediate length near the distal end is configured as an ablation structure and including a cannula lumen extending longitudinally through the length of the cannula; and an elongate stylet extending slidably through the cannula lumen and secured to the cannula between the ablation structure and the cannula distal end;

where the ablation structure includes a plurality of substantially parallel helical apertures disposed around a circumference of the outer cannula, the apertures extending through the cannula;

where the ablation structure is circumferentially expandable such that in a first state, when the distal cannula end is disposed at a maximum device-length distance from the proximal cannula end, the outer cannula is essentially cylindrical with a substantially uniform outer diameter along substantially its entire length; and in a second state, when the stylet and the secured cannula distal end are less than a maximum device-length distance from the proximal cannula end, the substantially parallel helical apertures of the ablation electrode are expanded and intervening portions of the cannula form an outer diameter greater than the outer diameter of cannula portions proximal of and distal of the ablation structure.

13. The device of claim 12, where the ablation device comprises an ablation structure selected from a microwave antenna; a radiofrequency electrode; an optical fiber; a light pipe; a tubular structure configured to allow closed or open passage therethrough of heated or cooled fluid with sufficient energy capacity to effect ablation; alternating current conductive wire; an ultrasound emitter; and any combination thereof.

14. The device of claim 12, further comprising a sheath through which a proximal length of the stylet longitudinally slidably extends.

15. The device of claim 14, where a proximal portion of the cannula is affixed to the sheath such that an actuation of the device comprising a longitudinal distal movement of the sheath relative to the stylet and/or a longitudinal proximal movement of the stylet relative to the sheath will foreshorten the cannula and effect transition from the first state to the second state.

16. A method of ablating tissue in a patient, the method comprising steps of:

introducing the device of claim 15 adjacent to a target site within a patient body; and actuating the device in a manner moving the sheath relative to the stylet and/or the stylet relative to the sheath to effect the second state.

17. The method of claim 16, wherein the step of introducing comprises directing the device through a working channel of an endoscope.

18. The method of claim 16, further comprising a step of directing energy through the cannula to ablate tissue in contact therewith.

19. The method of claim 18, where the energy is sufficient to necrotize animal tissue.

* * * * *